(12) United States Patent
Paulussen et al.

(10) Patent No.: US 10,722,127 B2
(45) Date of Patent: Jul. 28, 2020

(54) PHOTOPLETHYSMOGRAPHY DEVICE

(71) Applicant: KONINKLIJKE PHILIPS N.V., Eindhoven (NL)

(72) Inventors: Elvira Johanna Maria Paulussen, Eindhoven (NL); Olaf Thomas Johan Antonie Vermeulen, Oss (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 242 days.

(21) Appl. No.: 15/557,861

(22) PCT Filed: Feb. 26, 2016

(86) PCT No.: PCT/EP2016/054038
§ 371 (c)(1),
(2) Date: Sep. 13, 2017

(87) PCT Pub. No.: WO2016/146364
PCT Pub. Date: Sep. 22, 2016

(65) Prior Publication Data
US 2018/0049657 A1   Feb. 22, 2018

(30) Foreign Application Priority Data

Mar. 13, 2015  (EP) ..................................... 15158926

(51) Int. Cl.
*A61B 5/00* (2006.01)
*A61B 5/024* (2006.01)

(52) U.S. Cl.
CPC .......... *A61B 5/02427* (2013.01); *A61B 5/721* (2013.01); *A61B 2562/02* (2013.01); *A61B 2562/146* (2013.01)

(58) Field of Classification Search
None
See application file for complete search history.

(56) References Cited

U.S. PATENT DOCUMENTS

| | | | | |
|---|---|---|---|---|
| 5,759,156 A | * | 6/1998 | Hayakawa | A61B 5/02438 600/483 |
| 5,823,951 A | | 10/1998 | Messerschmidt | |
| 7,177,686 B1 | | 2/2007 | Turcott | |
| 8,768,424 B2 | | 7/2014 | Crowe | |
| 8,974,396 B1 | * | 3/2015 | Brady | A61B 5/02416 600/508 |
| 9,304,202 B2 | | 4/2016 | Deiwala | |
| 10,092,197 B2 | * | 10/2018 | Han | A61B 5/02427 |
| 2002/0151775 A1 | * | 10/2002 | Kondo | A61B 5/02438 600/344 |

(Continued)

FOREIGN PATENT DOCUMENTS

CN  104257378 A  1/2015
DE  102009017797 A1  10/2010

(Continued)

*Primary Examiner* — Joanne M Hoffman

(57) ABSTRACT

The invention relates to a photoplethysmography device (20) of the reflectance type, comprising a light source (4), a light sensor (5), and an interface layer (21). The interface layer (21) has a recess between the source (4) and the sensor (5) in order to prevent reflection losses between the device (20) and the skin and to prevent that light from the source (4) can reach the sensor (5) directly via the interface layer (21).

10 Claims, 3 Drawing Sheets

(56) References Cited

U.S. PATENT DOCUMENTS

| | | | |
|---|---|---|---|
| 2008/0097172 A1* | 4/2008 | Sawada | A61B 5/0261 600/310 |
| 2008/0097221 A1* | 4/2008 | Florian | A61B 5/02433 600/476 |
| 2008/0228089 A1* | 9/2008 | Cho | A61B 5/021 600/485 |
| 2014/0121471 A1* | 5/2014 | Walker | A61B 5/1128 600/301 |
| 2014/0127996 A1* | 5/2014 | Park | A61B 5/0205 455/41.1 |
| 2014/0142403 A1* | 5/2014 | Brumback | A61B 5/02433 600/324 |
| 2014/0275854 A1* | 9/2014 | Venkatraman | A61B 5/721 600/301 |
| 2014/0361147 A1* | 12/2014 | Fei | G01J 1/0407 250/206 |
| 2015/0282712 A1 | 10/2015 | Presura | |
| 2016/0058309 A1* | 3/2016 | Han | B61B 5/02427 600/479 |

FOREIGN PATENT DOCUMENTS

| | | |
|---|---|---|
| JP | 2004337605 A | 12/2004 |
| WO | 2011076886 A2 | 6/2011 |
| WO | 2013056379 A1 | 4/2013 |
| WO | 2013148753 A1 | 10/2013 |
| WO | WO-2013148753 A1 * | 10/2013 |

* cited by examiner

PHOTOPLETHYSMOGRAPHY DEVICE

This application is the U.S. National Phase application under 35 U.S.C. § 371 of International Application No. PCT/EP2016/054038, filed on Feb. 26, 2016, which claims the benefit of European Application No. 15158926.4, filed Mar. 13, 2015. These applications are hereby incorporated by reference herein.

FIELD OF THE INVENTION

The present invention relates to a photoplethysmography device of the reflectance type.

BACKGROUND OF THE INVENTION

US 2014/0275854 A1 describes a biometric monitoring device which is used to determine a user's heart rate by using a heartbeat waveform sensor and a motion detecting sensor. In some embodiments, the device collects collecting concurrent output data from the heartbeat waveform sensor and output data from the motion detecting sensor, detects a periodic component of the output data from the motion detecting sensor, and uses the periodic component of the output data from the motion detecting sensor to remove a corresponding periodic component from the output data from the heartbeat waveform sensor. From this result, the device may determine and present the user's heart rate.

Photoplethysmography (PPG) has been developed to measure variations in blood volume in human tissue and thereby detecting a pulse signal of the heartbeat.

Typically, in PPG monitoring, light emitting diodes (LEDs) with wavelengths between 520 nm (green) and 850 nm (infrared) are used in combination with a photodiode. Transmission type PPG measurements use typically wavelength ranges (e.g. 650-850 nm) longer than reflection type measurements (e.g. using wavelengths in the range 520-570 nm).

Theoretically, the reflectance measurement can be taken at any skin surface. Moreover, the path length of reflectance in tissue is much shorter than that of transmittance. Both in reflectance and transmittance measurements, the signal-to-noise ratio of the heartbeat is based on the amount of absorption of the blood.

Conventionally, transmittance measurements are in general more robust measurements in comparison to reflectance measurements. Therefore, less power of light is needed as for reflectance measurements. There are two reasons for this:

1. The optical path length through the blooded tissue in transmittance is larger than in reflectance, so the signal-to-noise ratio of the measured variation in blood during a heart pulse is larger in transmittance.

2. For transmittance measurements, mostly longer wavelengths are used, that penetrate deeper in the skin and have less interaction with scatter particles in the tissue.

Optical losses in PPG sensing are due to absorbance, reflectance and scattering in the sensor part and in the human tissue. In particular, optical losses take place between the light delivery system and the skin by reflectance losses when light penetrates from one media into the other and by surface scattering onto the skin.

Optical skin properties and skin morphology are used to simulate losses due to skin reflectance. The total reflectance at different angles of incidence has been simulated for different melanin fractions (skin type II and III on the Fitzpatrick scale) and the results are illustrated in FIG. 1 for a single wavelength 520 nm). It can be concluded that due to Fresnel losses on the skin surface, at high angle of incidence (>60°) the reflectance at the skin rapidly increases in respect to normal angle of incidence (0°).

A major performance indicator of PPG sensors is the so called modulation, which is defined as the ratio of the AC over DC signal (see FIG. 2). Here AC is the signal one wants to measure (the pulsating arterial blood fraction; i.e. the change in blood volume) and the DC part is the unwanted background signal. Although the use of the term DC indicates a signal of 0 Hz, it is actually a low frequency disturbance caused by, for example, leakage light shunted from source to detector without passing through tissue (static), variation of the previous term caused by motion (dynamic) and light reaching the detector reflected from any tissue/matter other than pulsating arterial blood (e.g. venous blood, fat, bone, water, cell membranes, etc).

Currently, in any PPG sensor the DC part is much larger than the AC part, therefore minimizing DC and/or maximizing AC is one of the major challenges in the design of a good PPG sensor.

The PPG signal reflects the blood movement in the vessels. The quality of the PPG signal depends amongst others on blood flow rate, skin morphology and skin temperature. Also the optical losses in the system determine the quality of the PPG signal.

SUMMARY OF THE INVENTION

It is an object of the present invention to address the optical efficiency of a photoplethysmography device of the reflectance type.

In a first aspect of the present invention a photoplethysmography device of the reflectance type is presented comprising at least one light source, at least one light sensor, and an interface layer, the interface layer being arranged for contacting the skin of a subject upon measurement, wherein the interface layer includes a recess between the light source and the light sensor, the recess preventing a light path between the light source and the light sensor within the interface layer.

The optical efficiency is amongst others determined by reflection losses when light penetrates from one media into the other and by scattering of the skin surface.

The inventors furthermore realized that a detrimental effect on the optical efficiency of the photoplethysmography device may be caused by light travelling within the interface between the light source and the light sensor, without passing through the subject. The present invention aims at preventing such effects by providing a recess blocking such path.

In a preferred embodiment, the interface layer is provided, on a face opposite to the light source and the light sensor, with at least one projection adjacent to the recess.

By means of the projection or protrusion, which is provided at the interface between—on the one side—the photoplethysmography device (including the light source and the light sensor) and on the other side the skin of the object, the size of the recess between the portions of the interface layer is increased, wherein furthermore an air gap is formed between the recess and the skin of the subject.

In a preferred embodiment, the recess is an elongated aperture or slit, which may additionally be curved.

The invention is not limited to particular shapes of the recess and it is also not necessary that the recess is completely surrounded by the remainder of the interface layer. The interface layer as such is not separated into different pieces by the recess so that handling of the interface layer, e.g. during production of the device, remains simple.

In a preferred embodiment, the interface layer includes a plate of thermoplastic transparent to the light used for photoplethysmography.

Examples of such thermoplastic material include Polymethylmethacrylate (PMMA) and polycarbonate.

In a preferred embodiment, the interface layer includes a rigid base layer and a soft coating or outer layer, the soft coating or outer layer arranged for contacting the skin of the subject.

The soft coating or outer layer provided on the rigid base layer allows for an improved contacting between the interface layer and the skin, wherein furthermore the coating or outer layer may also be used for further optical matching between the materials of the photoplethysmography device and the skin of the subject.

In a preferred embodiment, the interface layer includes or consists of a soft material arranged for contacting the skin of the subject.

Examples of such soft material includes silicone (in particular polydimethylsiloxane PDMS), rubber and the like.

In a preferred embodiment, the light source and/or the light sensor are provided with an encapsulation, the encapsulation of the light source and/or the encapsulation of the light sensor contacting the interface layer.

It is found by the inventors that the encapsulation allows for improvements in robustness of the photoplethysmography device and may have positive effects during manufacturing.

In a preferred embodiment, the photoplethysmography device further comprises a barrier wall arranged between the light source and the light sensor preventing a light path between the light source and the light sensor between the light source, the light sensor and the interface layer.

The barrier wall additionally prevents light travelling directly from the light source to the light sensor.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
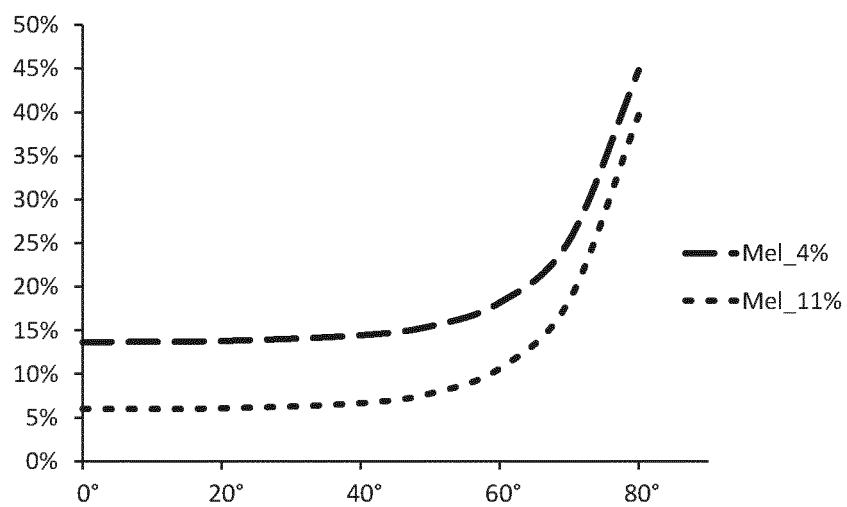
FIG. 1 illustrates a simulated reflectance at a wavelength of 520 nm for different angles of incidence and two different melanin fractions.

FIG. 1 illustrates a simulated reflectance at a wavelength of 520 nm for different angles of incidence and two different melanin fractions as discussed above.

Figure 2:
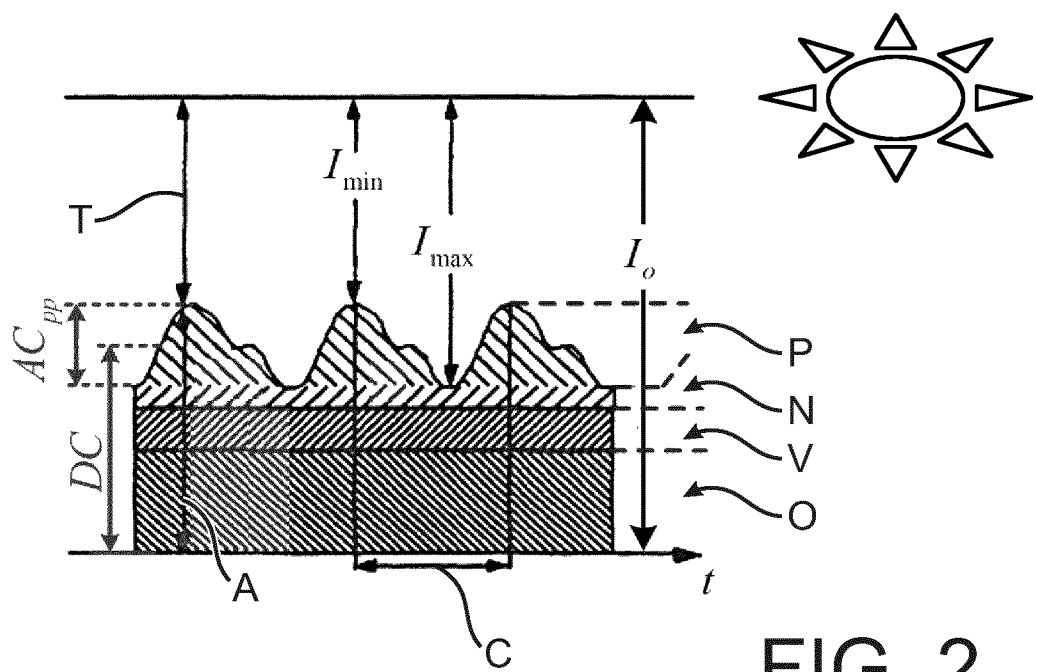
FIG. 2 illustrates influences on a photoplethysmography signal, FIGS. 3 a) to 3 e) show conventional set-ups for photoplethysmography devices, FIGS. 4 a) and 4 b) show schematically aspects of a photoplethysmography device in accordance with an embodiment of the invention.

FIG. 2 illustrates influences on a photoplethysmography signal. $I_0$ indicates the incident light, with T showing the transmitted light and A showing the absorbed light. The current absorbed amount of light results from absorption at pulsating arterial blood P, non-pulsating arterial blood N, venous blood V and other tissue O. As indicated above, the DC portion of the signal is not strictly constant and the AC portion (corresponding to the absorption by the pulsating arterial blood P) is the signal carrying the information used for photoplethysmography.

Figure 3:
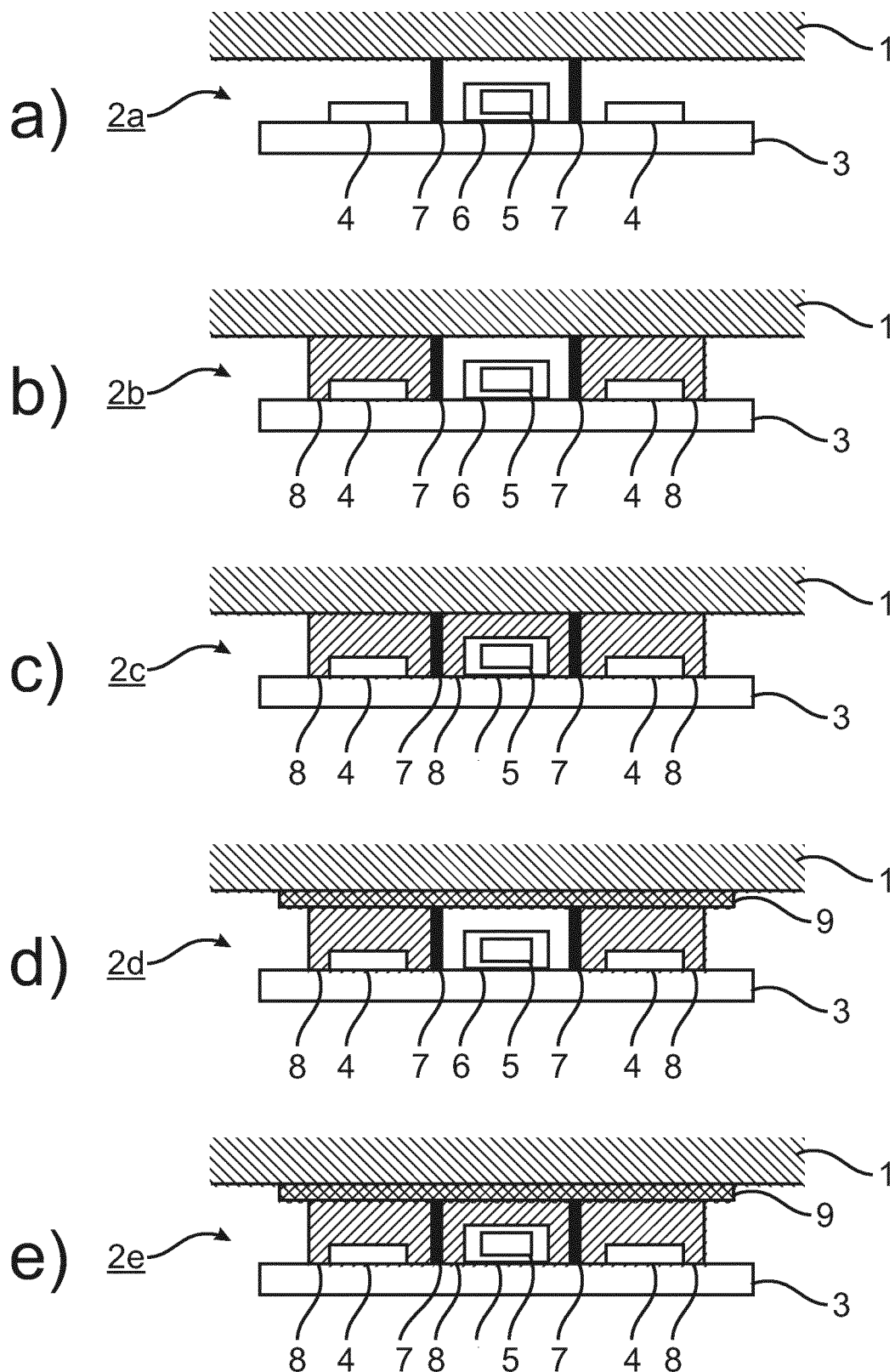

FIGS. 3 a) to 3 e) show conventional set-ups for photoplethysmography devices 2a to 2e.

The photoplethysmography devices 2a to 2e each include a basis 3, on which two LEDs 4 and a photodiode 5 are arranged. The photodiode 5 is embedded in a coating 6. Between the LEDs 4 and the photodiode 5 walls 7 are provided, respectively.

The photoplethysmography devices 2a to 2e are to be brought into contact with the skin of a patient 1 for measuring the vital signs.

For sake of lucidity and simplicity, further details of the patient (namely the blood vessels) and the photoplethysmography devices 2a to 2e are omitted from the figures. This also applies to FIGS. 4 a), 4b) and 5.

FIG. 3 a) illustrates a case where just the walls 7 are provided between the LEDs 4 and the photodiode 5 without further embedding or optical matching.

In FIG. 3 b), in contrast to FIG. 3 a), a case is shown where an epoxy filling 8 is provided around the LEDs 4. Thus epoxy filling 8 is advantageous in achieving a robust and manufacturable device design.

Also not explicitly shown in FIG. 3 b) and FIG. 3 c), it is to be noted that typically there is an air gap between the epoxy filling 8 and the skin of the patient 1.

In addition to the filling 8 around the LEDs 4, also the photodiode 5 and its coat 6 may be embedded into epoxy filling 8, as shown in FIG. 3 c).

The set-up illustrated in FIG. 3 d) differs from that shown in FIG. 3 b) in that additionally an interface layer 9 is provided for contacting the skin of the patient 3. In other words, between the elements of the photoplethysmography device 2b shown in FIG. 3 b) (which are also provided in the photoplethysmography device 2d) and the skin the interface layer 9 is provided.

Similarly, the arrangements shown in FIGS. 3 c) and 3 e) differ in the addition of the interface layer 9.

In the case of FIGS. 3 a) to 3 c), due to total internal reflection caused by the different refractive indices of the skin and the material between the skin and the LEDs 4 (i.e. either air in case of FIG. 3 a) or epoxy 8 in case of FIGS. 3 b) and 3 c)), light is lost.

In the case of FIGS. 3 d) and 3 e), there is no change in refractive indices (or at least only a reduced change) between the epoxy 8 and the interface layer 9 and/or the interface layer 9 and the skin, and losses otherwise caused by total internal reflection are reduced by the interface layer 9.

With an interface layer 9 provided between the light delivery system (i.e. the LEDs 4) and the skin and also between the skin and the light acceptance system (i.e. the photodiode 5), losses caused by reflectance at the surfaces are reduced and the overall efficiency of the system is increased.

From modelling, the inventors have derived that an optical interface between light delivery system and skin increases efficiency performance with a factor of 2 in the set-up shown in FIG. 3 d) and a factor of more than 4 in the set-up shown in FIG. 3 e). Taking the arrangement shown in FIG. 3 a) as reference (value 1), the relative response of the photodiode is 0.7 for the set-up shown in FIG. 3 b), 0.6 for the set-up shown in FIG. 3 c), 2.0 for the set-up shown in FIGS. 3 d) and 4.2 for the set-up shown in FIG. 3 e). The value 0.7 for the set-up shown in FIGS. 3 b) and 0.6 for the set-up shown in FIG. 3 c) are due to air gaps between the epoxy 8 and the skin of the patient 1.

It is assumed that the gain in efficiency by the optical interface between the light delivery system and the skin is caused by two aspects:

1. Total internal reflection losses on the epoxy 8 are prevented or at least reduced by the contact epoxy 8—optical interface layer 9.

2. Fresnel reflections on the skin (see also FIGS. 1 and 2) are prevented or at least reduced by the contact optical interface layer 9—skin.

It is further assumed that the gain in efficiency by the optical interface between the skin and light acceptance system is caused by:

1. Total internal reflection losses on the skin are prevented or at least reduced by the contact skin—optical interface layer 9.

2. Fresnel reflections on the diode (cover plate) are prevented or at least reduced by the contact optical interface layer 9 diode—5/6.

Considering a case with the refractive index of the epoxy 8 being 1.41, the refractive index of air between the epoxy 8 and the skin of the patient 1 being 1.0 and the refractive index of the skin (and tissue) of the patient being 1.43, losses result from Fresnel reflections at the interface air/skin and from total internal reflection at the interface epoxy 8/air. In a case, where the interface layer 9 has substantially the same refractive index as the epoxy (i.e. 1.41) but no air gap is present, losses result only from the Fresnel reflections at the interface between the interface layer 9 and the skin, while there is substantially no total internal reflection. If was further found that generally the losses resulting from Fresnel reflections at the interface air/skin are higher than losses resulting from the Fresnel reflections at the interface between the interface layer 9 and the skin.

Figure 4:
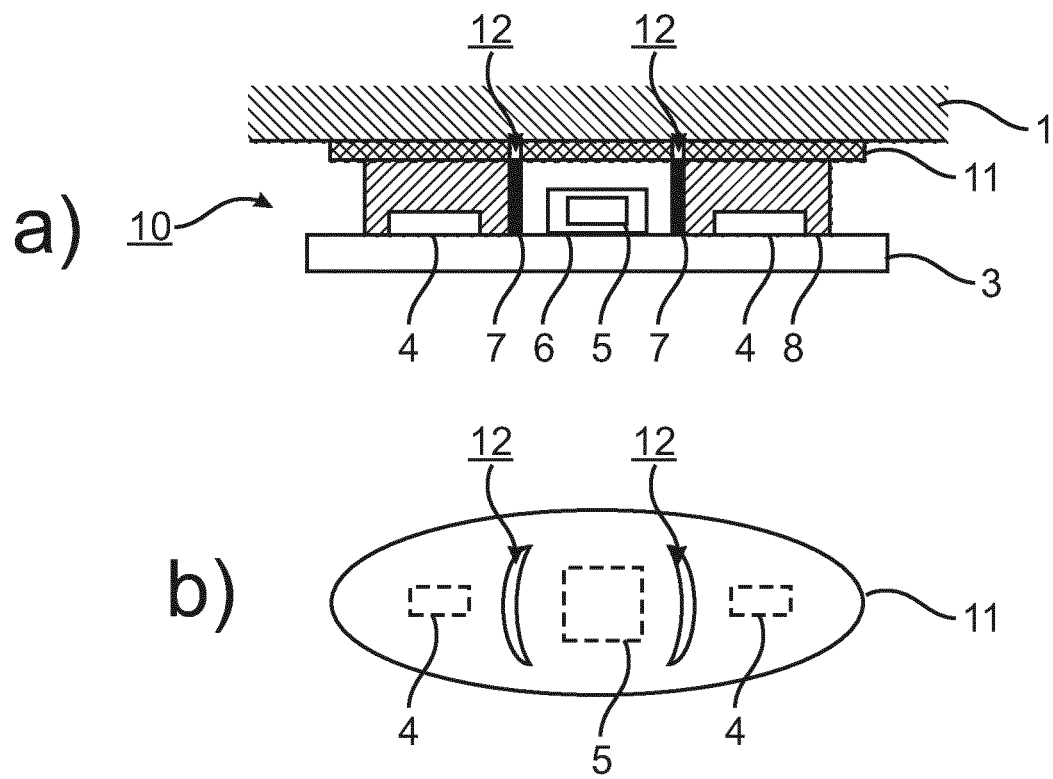

FIGS. 4 a) and 4 b) show schematically aspects of a photoplethysmography device in accordance with an embodiment of the invention.

The embodiment shown in FIGS. 4 a) and 4 b) provide for an optical PPG device 10 to measure vital signs, comprising at two light sources in the form of LEDs 4 and one photodiode 5, with an optical interface layer 11 between the device and skin, wherein the interface layer 11 has recesses 12 between the light sources 4 and the photodiode 5 in order to prevent reflection losses between the photodiode 5 and the skin and to prevent that light from the light sources 4 can reach the photodiode 5 directly via the interface layer 11 (without passing through the patient 3). The material of the interface layer 11 is a hard (thermo)plastic plate (e.g. polycarbonate or PMMA). The plate 11 can also be coated (not shown) with a soft material on the skin side to further improve optical contact. Alternatively, the interface layer may be formed of a soft material like PDMS or a suitable rubber.

The basic structure of the photoplethysmography device 10 corresponds to that shown in FIG. 3 d). However, the interface layer 11 is not continuous as the interface layer 9 but includes recesses 12 (elongated and curved apertures as shown in FIG. 4 b)) which are provided to prevent light travelling within the interface layer 11 from the area between the LEDs 4 and the skin to the area between the skin and the photodiode 5, where otherwise such light bypassing the trip through the tissue would have detrimental effects in reducing the signal-to-noise-ratio or the AC-to-DC ratio (see FIG. 2).

FIG. 4 b) shows an example of such interface layer 11, wherein the relative positions of the LEDs 4 and the photodiode 5 with respect to the recesses or apertures 12 are also shown.

Figure 5:
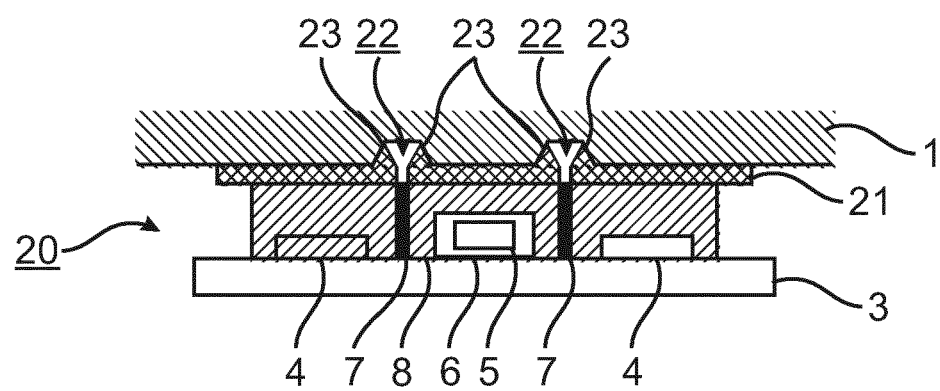
FIG. 5 shows schematically a photoplethysmography device in accordance with another embodiment of the invention.

FIG. 5 shows schematically a photoplethysmography device in accordance with another embodiment of the invention.

As with FIG. 4 a) and FIG. 3 d), also in this case the basic structure of the photoplethysmography device 20 corresponds to that shown in FIG. 3e). Again, as with the above embodiment, the interface layer 21 is not continuous and includes recesses 22 which are provided to prevent light travelling within the interface layer 21 from the area between the LEDs 4 and the skin to the area between the skin and the photodiode 5, where otherwise such light bypassing the trip through the tissue would have detrimental effects in reducing the signal-to-noise-ratio or the AC-to-DC ratio (see FIG. 2).

In addition to the situation already discussed in regard to the above embodiment, the recesses 22 are enclosed by a pedestal or projection 23 on each side of the recess 22, thus creating an enlarged air gap at the skin between the light delivery system and the light acceptance system.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single device or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A photoplethysmography device of the reflectance type, comprising:
   at least one light source;
   at least one light sensor;
   at least one barrier wall; and
   an interface layer spaced apart from and covering the at least one light source and the at least one light sensor, the interface layer arranged for contacting the skin of a subject upon measurement, wherein the interface layer includes a recess between the at least one light source and the at least one light sensor, the recess preventing a light path between the at least one light source and the at least one light sensor within the interface layer.

2. The photoplethysmography device according to claim 1, wherein the interface layer is provided, on a face opposite to the at least one light source, and the at least one light sensor, with at least one projection adjacent to the recess.

3. The photoplethysmography device according to claim 1, wherein the recess is an elongated aperture or slit.

4. The photoplethysmography device according to claim 1, wherein the interface layer includes a plate of thermoplastic transparent to the light used for photoplethysmography.

5. The photoplethysmography device according to claim 1, wherein the interface layer includes or consists of silicone or rubber arranged for contacting the skin of the subject.

6. The photoplethysmography device according to claim 1, wherein the at least one light source and/or the at least one light sensor are provided with an encapsulation, the encapsulation of the at least one light source and/or the encapsulation of the at least one light sensor contacting the interface layer.

7. The photoplethysmography device according to claim 1, further comprising a barrier wall arranged between the at least one light source and the at least one light sensor preventing a light path between the at least one light source and the at least one light sensor between the at least one light source, the at least one light sensor and the interface layer.

8. A photoplethysmography device of the reflectance type, comprising:
   a light source and a light sensor arranged on a base;
   a barrier wall arranged between the light source and the light sensor;
   an interface layer spaced apart from the light source, the light sensor, and the base, the interface layer arranged for contacting the skin of a subject upon measurement; and
   a recess arranged in the interface layer in line with the barrier wall, the recess preventing a light path between the light source and the light sensor.

9. The photoplethysmography device according to claim 8, wherein the barrier wall extends between the base and the interface layer.

10. A photoplethysmography device of the reflectance type, comprising:
    a first side arranged to contact the skin of a subject;
    a second side, opposite the first side;
    at least one light source arranged on the second side;
    at least one light sensor arranged on the second side; and
    an interface layer including a recess arranged on the first side, wherein the interface layer and the recess are separated from the at least one light source and the at least one light sensor by a barrier wall, and the recess is between the at least one light source and the at least one light sensor to prevent a light path between the at least one light source and the at least one light sensor within the interface layer.

* * * * *